(12) United States Patent
Steen

(10) Patent No.: US 7,270,833 B2
(45) Date of Patent: Sep. 18, 2007

(54) CARDIOPLEGIC SOLUTION

(75) Inventor: Stig Steen, Lund (SE)

(73) Assignee: Jolife AB, Lund (SE)

( * ) Notice: Subject to any disclaimer, the term of this patent is extended or adjusted under 35 U.S.C. 154(b) by 441 days.

(21) Appl. No.: 10/344,038

(22) PCT Filed: Aug. 7, 2001

(86) PCT No.: PCT/SE01/01719

§ 371 (c)(1),
(2), (4) Date: Jul. 21, 2003

(87) PCT Pub. No.: WO02/11741

PCT Pub. Date: Feb. 14, 2002

(65) Prior Publication Data

US 2004/0018245 A1 Jan. 29, 2004

Related U.S. Application Data

(60) Provisional application No. 60/230,812, filed on Sep. 7, 2000.

(51) Int. Cl.
*A01N 59/00* (2006.01)
*A01N 59/06* (2006.01)
*A01N 59/24* (2006.01)
*A61K 33/00* (2006.01)
*A61K 33/10* (2006.01)

(52) U.S. Cl. ............... 424/600; 424/610; 424/686; 424/715

(58) Field of Classification Search .......... None
See application file for complete search history.

(56) References Cited

U.S. PATENT DOCUMENTS 5,552,267 A * 9/1996 Stern et al. ............... 435/1.1
6,449,507 B1 * 9/2002 Hill et al. ..................... 607/9

FOREIGN PATENT DOCUMENTS

DE 1176651 * 8/1964

OTHER PUBLICATIONS

"Conversion of Postischemic Ventricular Fibrilation With Intraaortic Infusion of Potassium Chloride," Eivind Ovrum et al, Ann Thorac Surg, vol. 60, No. 1, 1995.
19th Congress of the Scandinavian Society of Anaesthesiologists in Linkoping, Ssweden, Jun. 29-Jul. 3, 1987, "Acta Anaesthesiologica Scandinavia," Supplementum 86, vol. 31, 1987, L. Bjella et al, "Potassium Chloride Used to Prevent Ventricular Fibrillation at Reperfusion in Open Heart Surgery," No. 11.
*Heart*, vol. 80, No. 4, 1998, D.A. Chamberlain, "Antiarrhythmic Drugs in Resuscitation".
The Canadian Journal of Surgery, vol. 23, No. 2, Mar. 1980, A. Addetia et al, "Perfusion in Cardioplegia: an Experimental Study".
Anaesthesiol Reanimat, vol. 18, No. 6, 1993, Von H. Wulf et al, "Kaliumsubstitution bei koronarchirgischen Eingriffen: K+-Mg++- Aspartat-Komplex (Inzolen) versus Kaliumchlotid,".
The American Journal of Cardiology, vol. 33, No. 1, Jan. 1974, John C Fischer et al, "Studies on Ventricular Defibrillation".
File WPI, Derwent Accession No. 1996-096008, Novos Blood Circulation Pathology Inst, "Protecting Myocardium in Heart Operation-with Perfusion-free Hypothermia by Introduction of Cooled Cardioplegic Soln.Contg. Potassium".
File WPI, Derwent Accession No. 2000-557077, Blood Circulation Pathology Res Inst, "Method of Prophylaxis Heart Rhythm Disorder in Cardiosurgery Operations".
Susan Budavari et al, "The Merck Index, eleventh edition," 1989, Merk & Co., Inc., p. 1211-1213, No. 7580, 7586, 7599, 7601; p. 1216, No. 7647.

* cited by examiner

*Primary Examiner*—David M. Naff
*Assistant Examiner*—Deborah K. Ware
(74) *Attorney, Agent, or Firm*—Browdy and Neimark, PLLC

(57) ABSTRACT

Use of potassium for the production of a cardioplegic solution for the prevention of stone heart development during acute cardiac ventricular fibrillation in connection with cardiopulmonary resuscitation is described, as well as a cardioplegic solution comprising potassium and a method for the prevention of stone heart developement during acute cardiac ventricular fibrillation in connection with cardiopulmonary resuscitation.

12 Claims, 2 Drawing Sheets

CPR with potassium chloride and A-V ECMO

CPR with potassium chloride and A-V ECMO

CARDIOPLEGIC SOLUTION

The present application claims priority from, inter alia, the provisional U.S. application 60/230,812 filed Sep. 7, 2000.

FIELD OF THE INVENTION

The present invention relates to use of potassium ions for the production of a medicament for the prevention of stone heart development during acute cardiac ventricular fibrillation in connection with cardiopulmonary resuscitation (CPR), to a cardioplegic solution comprising potassium and to a method for the prevention of stone heart development during acute cardiac ventricular fibrillation.

This application is a 371 of PCT/SE01/01719 filed Aug. 7, 2001.

BACKGROUND ART

In the Western world 30% of all deaths is due to ischemic heart disease, i.e. coronary atherosclerosis. In about 70% of these deaths acute ventricular fibrillation causes the circulatory arrest. In about 30% of these deaths electromechanical dissociation, i.e. heart arrest without ventricular fibrillation, is the reason for acute death. Most of these deaths occur outside hospitals. Before effective cardiopulmonary resuscitation can be initiated several minutes without any form of cardiac massage often occur. When the heart does not receive blood and energy, the ionic pumps of the heart muscle cells become more and more inefficient which results in an increase of the intracellular concentration of calcium. When the intracellular concentration of calcium increases, the contractile state of the heart increases. Ultimately, a condition described as "stone heart" or ischemic contraction of the heart occurs. Cooley described in 1972 an ischemic contraction condition of the heart and called it "stone heart". He described the heart in these cases as small and irreversibly contracted, and it appeared to be literally frozen in systole, as certain protein structures of the heart muscle cells are irreversibly disrupted. If such a condition occurs during cardiopulmonary resuscitation, it is not possible to perform effective external or internal heart massage, because there will be no lumen left in the ventricles and therefore no possibility for the blood to pass through the heart. The clinical result of cardiopulmonary resuscitation as it is practiced today for patients dying outside hospital is very poor, with a mortality of around 97-98%. In most cases, it is not possible to perform effective heart massage 20 minutes after the cardiac arrest, and in some countries there is a recommendation that if you can not bring the heart to work within 20 minutes, you may declare the patient dead and stop all types of cardiopulmonary resuscitation.

When a patient's heart today stops outside a hospital the general population has been trained in doing cardiopulmonary resuscitation. This consists of mouth to mouth blowing in of expiratory air and manual compression of the chest, i.e. 5 compressions of the chest, followed by 1 inblow of expiratory air or 2 inblows and 15 chest compressions. A cardiac output of about 10-15% of the normal output in rest may be obtained by manual external chest compression, and this low output is not enough to give the heart enough blood to survive more than for a few minutes. If especially well trained personnel arrive to the accident place, defibrillation of the heart is tried if ventricular fibrillation is diagnosed, and the patient is intubated and ventilated with 100% oxygen. It is also very difficult to transport a patient having circulatory arrest into hospital because it is not possible to perform effective external chest compression during transportation in the ambulance. For that reason most of these patients are declared dead if they not can be saved on the accident place. Thus, there is a great world-wide need to develop methods and means for treatment of such patients also under transport until access to adequate artificial circulation means at hospitals or other medical centres.

OBJECT OF THE INVENTION

The object of the present invention is to eliminate the above-mentioned current drawbacks and shortcomings in connection with treatment of acute cardiac ventricular fibrillation during CPR and thereby save lives or organs for transplantation.

This object is achieved by use of potassium ions for the production of a cardioplegic solution as defined by way of introduction in a method for the prevention of stone heart development during acute cardiac ventricular fibrillation, said use and method having the features defined in the appended independent claims.

The present invention also refers to a kit for cardiopulmonary resuscitation comprising said cardioplegic solution.

Further advantages and other features appear from the description and the appended subclaims.

DESCRIPTION OF THE DRAWING(S)

SUMMARY OF THE INVENTION

Figure 1:
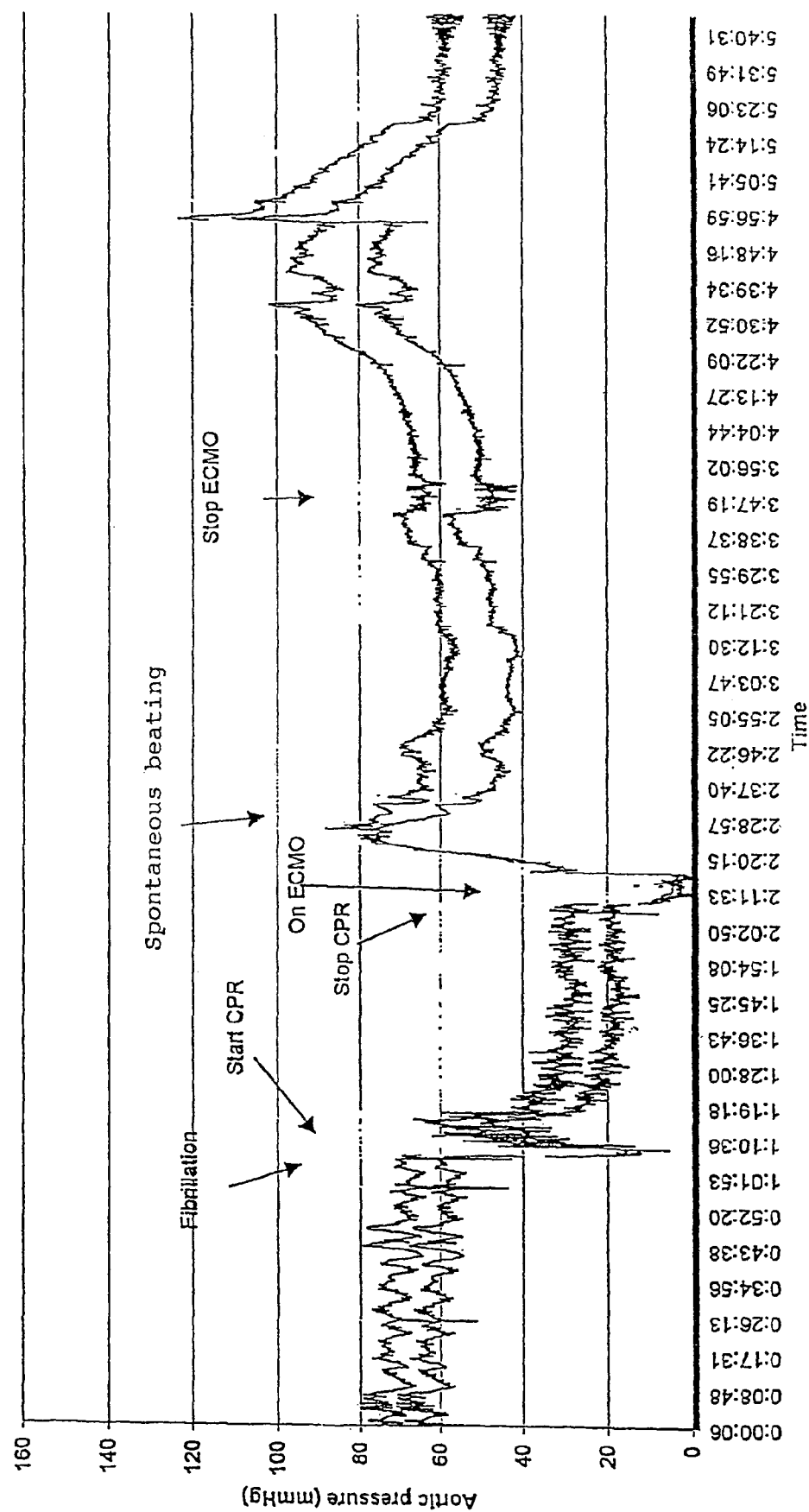
FIG. 1 illustrates the effect of CPR with potassium chloride and V-A ECMO on the aortic pressure during an experiment with pigs.

Thus, the active ingredient in the cardioplegic solution according to one aspect of the present invention is potassium, more precisely potassium ions. The concentration of potassium depends on whether the cardioplegic solution is to be injected directly into the heart or administered as an infusion, e.g. via a vein catheter.

The potassium ion concentration reaching the heart, i.e. the coronary vessels, must be 12-30 mM, preferably 16-22 mM, with a view to switching off the electric activity of the heart, thereby avoiding the undesired stone heart condition and allowing heart compressions. By making the heart muscle cardioplegic, i.e. relaxed, the wall tension of the heart is lowered to near zero, and coronary perfusion will be obtained at much lower coronary perfusion pressures. Thus, in the case when the cardioplegic solution initially is to be injected directly as a booster into the heart, the potassium ion concentration in the cardioplegic solution must be 12-30 mM, preferably 16-22 mM, and most preferably approximately 20 mM, i.e. no dilution effects occur. After the initial booster injection, i.e. after approximately 10-60 s, normally 30 s, the cardioplegic solution according to the present invention should be administered continuously as a maintenance dose to the heart, e.g. as an infusion at the injection site. The potassium ion concentration reaching the heart during the continuos administration must also be 12-30 mM, preferably 16-22 mM. In the case when the cardioplegic solution is to be initially administered as an infusion solution, the potassium ion concentration normally is 12-140 mM due to the dilution effect in the aortic blood on the way to the heart. Further, after the initial infusion having a high potassium ion concentration, the cardioplegic solution should be continuously administered in the form of an infusion, i.e. after approximately 30 s, followed by incremental decreases of the potassium ion concentration, while maintaining the potassium ion concentration in aortic blood between 15 and 20 mM.

The expression "injected directly into the heart" as used throughout the patent application text means that the cardioplegic solution is injected directly in the coronary vessels, e.g. the coronary arteries or sinus coronarius. Due to a slight dilution effect the potassium ion concentration of the cardioplegic solution should be a bit higher than 12-30 mM when injected directly into the left ventricle. No or negligible dilution effects occur when injected directly in the coronay vessels.

In some circumstances a potassium ion concentration of up to 140 mM is applicable, but in such a case high amounts of vasodilator has to be present to compensate for the vasoconstrictive effects.

When administrated as an "infusion solution" on the venous side, the best results are obtained if the cardioplegic solution is administered via a central venous catheter into the right atrium, the right ventricle or arteria pulmonaris. Peripherally induced infusion is less applicable.

It should also be noted that a lower temperature of the cardioplegic solution generally requires a lower potassium ion concentration to obtain adequate cardioplegia.

When the cardioplegic solution according to the present invention is administered as an infusion, the potassium ion concentration is initially high, if the infusion is given into the patient on the venous side.

Thereafter, the potassium ion concentration is incrementally decreased due to a saturation effect in the blood, in which a potassium ion concentration of 15-20 mM is desired to be continuously maintained. Said concentration normally varies between 12 and 140 mM dependent on such factors as the administration flow rate, e.g. depending on the infusion pumps used; the total blood volume of the patient and the amount and type of vasodilator administrated. Thus, the initial potassium ion concentration and the continuous decrease thereof during the infusion treatment is established by the practitioner dependent on the factors mentioned above.

The cardioplegic solution according to the present invention also contains a vasodilator, i.e. a blood vessel expanding agent, due to the undesired vasoconstrictive effect obtained by the administration of potassium to the heart. Non-limiting examples of the vasodilator are papaverin, magnesium, nitroglycerin, nifedipin, and nitroprusside. The most preferred vasodilator is papaverin. The concentration of the vasodilator depends on the vasodilator used, and is preferably papaverin in an amount of 40-120 mg.

A combination of two or more of the above-mentioned vasodilators may also be used. Alternatively, the vasodilator may be present in a solution to be separately administered, however at the same time or somewhat in advance in relation to the potassium containing cardioplegic solution.

Further, the cardioplegic solution according to the present invention also contains one or more physiologically acceptable and compatible components, e.g. anions originating from the potassium salt which is dissolved during the preparation of the cardioplegic solution. Non-limiting examples of anions are chloride, acetate, lactate phosphate, carbonate, and bicarbonate. A combination of two or more types of anions may be present in the cardioplegic solution. Preferably, chloride ions are present in the cardioplegic solution, i.e. potassium chloride is initially dissolved during the preparation. Other physiologically acceptable components may also be present. Bicarbonate ions also have a buffering action. If the above-mentioned lower potassium ion concentration limits would be further lowered, no satisfactory cardioplegic effects would be attained. If the above-mentioned upper concentration would be exceeded, vasoconstriction problems might occur if not an adequate dosis of papaverin or another vasodilator is administered simultaneously.

The pharmaceutically acceptable medium, in which the components described above are present, is preferably water.

The cardioplegic solution according to the present invention is conveniently commercialised and stored in the form of a solution in a container, preferably plastic bags or bottles. E.g., depending on whether the cardioplegic solution is to be used as an injection booster solution, an infusion booster solution, or as a continuously administrated solution after the initial injection or infusion, the potassium ion concentration may be predetermined and the container be labelled with the potassium ion concentration in question. Alternatively, one standard potassium ion concentration of the cardioplegic solution is used, and the concentration thereof reaching the heart is regulated by the administration flow rate.

In another embodiment the present invention refers to a kit containing the cardioplegic solution in a convenient container or more than one container optionally having different labels depending on the potassium ion concentration to be used. Further, the kit may contain equipment normally used for injection and/or infusion, e.g. needles, cannulas, catheters, etc.

Alternatively, the potassium containing solution and the vasodilator containing solution may comprise different components of the kit and be present in different containers, however intended to be used simultaneously or essentially simultaneously.

In one aspect the present invention also relates to the use of potassium for the production of a cardioplegic solution for the prevention of stone heart development during acute cardiac ventricular fibrillation in connection with cardiopulmonary resuscitation, wherein potassium in the form of a salt with one or more kinds of anions is dissolved in a pharmaceutically acceptable medium optionally together with a vasodilator, wherein the potassium ion concentration is 12-30 mM in the case when the cardioplegic solution is to be initially injected as a booster directly into the heart, and 12-140 mM in the case when the cardioplegic solution is to be initially administered as a infusion.

It has not been known before to use potassium ions for the prevention of the fatal stone heart condition during CPR treatment of acute cardiac ventricular fibrillation. Even though it is previously known to administer potassium, e.g. potassium chloride, during intentional cardioplegia in connection with open heart surgery, such as heart transplantations and coronary bypass surgery, wherein the purpose of the potassium administration only is to keep the heart non-beating without damage during the operation phase, the present inventor has surprisingly found, after long term studies, that the addition of potassium to the heart during CPR of experimental animal suffering from acute ventricular fibrillation eliminates the development of stone heart, thereby making it possible to recover all hearts even after one hour of heart massage. Successful prolonged heart massage has previously not been possible, inter alia due to lack of reliable CPR devices at the accident place and during the transport to hospitals. Also, the present invention is paradoxal and goes against the common sense, i.e. that the heart electricity first is practically abolished or "killed" with a view to revive it thereafter.

Thus, the present invention is applicable at the location for the acute cardiac ventricular fibrillation and during the transport of the patient to a hospital. Further, the combined use of a heart-lung machine is not required before arrival at the hospital. Instead, it suffices with the combined use of an effective heart compression device, as exemplified below ("Lucas").

In still another aspect the present invention relates to a method for the prevention of stone heart development during acute cardiac ventricular fibrillation, wherein a cardioplegic solution as defined above is administrated to the patient as a booster solution via direct injection into the heart, more precisely the coronary vessels, or in the left ventricle, or via intravenous infusion, each followed by a continuous administration of the potassium containing cardioplegic solution in the latter case while maintaining the potassium ion concentration in the patient's aortic blood between 15 and 20 mM during a sufficient time period with a view to preventing development of stone heart and allowing compressions of the heart during the CPR. In such a way several lives can be saved. Optionally, the method according to the present invention also provides a possibility to maintain the circulation in the body of a patient the life of which later on may turn out to be impossible to save. By maintaining the circulation and thereby the blood supply to the organs in the body, these organs might be a subject for transplantation, thereby saving the lives of other patients. This aspect might be applicable in the future when or if persons in advance decide to make their organs after death available for transplantation.

In accordance with one embodiment of the method according to the present invention, the potassium ion concentration in the heart after the administration of the cardioplegic solution may be normalised or reduced towards normal levels by the administration of insulin and glucose in the form of an infusion solution, whereby the potassium ion concentration is reduced towards a normal level. This administration is also beneficial for the reconditioning of the heart. Normally the amount of insulin and glucose added is approximately 100 international units of short term acting insulin and 10 ml 30% or 50% glucose, respectively, and the solution thereof is infused to the heart during a convenient time period, normally about 10-60 s, preferably about 30 s.

According to the prevailing guidelines defibrillation should be performed first in the treatment of ventricular fibrillation However, if possible, simultaneous chest compression should also be given. This is normally impossible in practice, mostly depending on that the patient becomes electrically conductive, thereby creating a risk for another person being in contact with the patient being defibrillated to be stricken with ventricular fibrillation. However, this combined treatment is facilitated by use of the so-called "Lucas" (Lund University Cardiac Assist System), a CPR device produced by Jolife AB, Sweden. This device comprises a compression-decompression means to be operated together with a defibrillator means at the same time. Further, this device provides the possibility to be mounted directly on a stretcher, thereby allowing the correct treatment, i.e. both defibrillation and compressions at the same time, without any risk for CPR team members. The kit according to the present invention comprising the potassium cardioplegic solution according to one aspect of the present invention is intended to be used as a complement to the "Lucas" device, but also to other similar devices used at present both medical devices for internal or external compressions and decompressions.

In the case of acute cardiac ventricular fibrillation due to cardiac infarct the heart of the patient is, during correct treatment, subjected to constant compressions in combination with defibrillation intervals. If not defibrillation performed under up to about 20 min is able to break the ventricular fibrillation and restore the heart rhythm, today no further treatment is made and the patient's life is regarded to be impossible to save, particularly if the development of the fatal stone heart condition has been initiated. This condition normally starts about 20 min after the circulatory arrest, but may vary dependent on several factors, and is continuously aggravated until the final contracted state without or with minimal lumen is reached.

By the administration of the cardioplegic solution according to the present invention during the CPR program and also up to the point when the defibrillation gives no response, the stone heart condition can be prevented by switching off or considerably reducing the electric activity of the heart. It is also possible to administrate the cardioplegic solution according to the present invention, i.e. at a hospital or other place having adequate CPR competence and devices, with a view to remove ventricular fibrillation which can not be defibrillated and thereby the risk for stone heart and also allowing the possibility of manual heart compressions while waiting for the access to a heart-lung machine. This might be the situation when acute ventricular fibrillation occurs, e.g. during PCTA treatment (percutaneous transluminal coronary angioplasty) which may induce ventricular fibrillation due to a flow of blood into an ischaemic area.

However, it is important that ventricular fibrillation has been diagnosed, e.g. by use of electrocardiography before the administration of the cardioplegic solution according to one aspect of the present invention takes place, otherwise said administration could be directly fatal.

Experiments

Due to the access to the new external chest compression machine, "Lucas", we have run extensive experiments in pigs. Until now we have run experiments in 5 years and used over 800 pigs. This new machine is much more efficient than manual compression of the chest. About 30% of the pigs with ventricular fibrillation survived 1 hour of external heart massage with the machine in normothermia. With manual compression no pigs survived 15 minutes. The pigs which did not survive showed a condition similar to stone heart at autopsy, the hearts were in an extreme contraction state and they had almost no lumen in the left ventricle, so the blood could not simply pass through such a contracted heart. We noticed that this started to happen after 15 minutes. The first 15 minutes all pigs survived with the "Lucas" machine, but after 20 minutes some pigs started to die off and after 60 minutes 70% of the pigs died (i.e. the return of spontaneous circulation was not possible to achieve by defibrillation. At autopsy the pigs that have died showed this condition described by Cooley as stone heart.

The idea then came up that if cardioplegia is induced to the heart during heart arrest, it would be possible to eliminate this stone heart condition and make 100% of the hearts survive 60 minutes of heart compression. In clinical heart surgery we routinely use potassium to accomplish depolarisation and cardioplegia. We induced ventricular fibrillation in pigs and then induced cardioplegia in the form of potassium chloride into a central venous needle or even directly into the left ventricle, thereby inducing cardioplegia. By a continuous infusion of potassium chloride we kept the heart in a cardioplegic condition. Then heart compressions for 1 hour were possible, without the development of stone heart. After 60 minutes we cannulated the pig in the femoral artery and vein and established an extracorporeal membrane oxygenation (ECMO). Then, we washed away the potassium chloride by filtration, and the heart started to beat spontaneously again. When cardioplegia is induced in a heart at normotermia, 90% of the need for oxygen is eliminated, and the heart is arrested in a relaxed condition. Such a heart is very easy to perform external or internal heart massage on.

Potassium also creates vasoconstriction in the concentrations needed to obtain cardioplegia. This potassium induced vasoconstriction can be eliminated by vasodilators, e.g. by papaverine. By giving insulin and glucose it is also possible to reduce the potassium ion concentration. Administration of insulin and glucose are also beneficial for the reconditioning of the heart.

An experiment performed is described in detail below.

Internal Cardiopulmonary Resuscitation by Continuous Left Ventricle Infusion of Potassium Chloride The purpose of the experiment was to evaluate the effects of continuous potassium chloride infusion during internal CPR with a catheter inserted into the left ventricle and to investigate the need for ECMO (extracorporeal membrane oxygenation) after high dose potassium chloride treatment during CPR, to obtain return of ROSC after prolonged CPR.

The haemodynamic parameters continuously was measured and stored as mean values every 5 second. Blood gases was analyzed with a Radiometer™ ABL 555® blood gas machine. Drug administration (Addex® potassium 4 mmol/ml, Fresenius Kabi, Uppsala, Sweden. 40 mg/ml papaverin, NM Pharma, Stockholm, Sweden.) during CPR was given according a specific protocol.

The test parameters were selected to meet the International Organization of Standardization (ISO) requirements for biological evaluation of medical devices (10993-4: 1992 (E)). The following data parameters were measured and stored as mean values every 5 seconds throughout the experiment:

ECG, arterial pressure (SAP/MAP/DAP), central venous pressure (CVP), coronary perfusion pressure (CPP), carotid flow (CF), temperature, urine production (every 15 min), and blood gases.

The blood gas (Radiometer™, ABL 555®) data parameter were measured and stored intermittently or written down by hand throughout the experiment.

Electrically ventricular fibrillation was induced electrically in healthy test pigs (25-80 kg in body weight) at normothermic conditions (a body temperature of 38° C.). After 90 seconds of untreated ventricular fibrillation internal heart massage started manually and continued for 60 min. At the same time a booster injection of 10 ml potassium (Addex® potassium 4 mmol/ml, Fresenius Kabi, Uppsala, Sweden) and 3 ml papaverin sulfate (Papaverin 40 mg/ml, NM Pharma, Stockholm, Sweden) was given. Directly after a potassium infusion (Addex® potassium 4 mmol/ml, Fresenius Kabi, Uppsala, Sweden) was started (100 ml/h for 20 min, 50 ml/h for 20 min, 20 ml/h for 20 min). Thus, the potassium ion concentration of the aortic blood, i.e. the blood entering the heart, was kept at 15-20 mM, which is enough for maintaining cardioplegia. After 60 minutes of resuscitation V-A (venoarterial) ECMO was established and by ultrafiltration the serum potassium ion concentration was reduced towards normal levels. The heart started to beat spontaneously when the serum (S) potassium ion concentration decreased to less than 8 mM.

| CPR in a 25 kg Swedish domestic pig | | | | |
|---|---|---|---|---|
| Samp. No. | Exp. Time | Date | Time | Event |
| 774 | 1:06:56 | 00.05.15 | 10:35:00 | fibrillation induced |
| 791 | 1:08:26 | 00.05.15 | 10:36:30 | 3 ml papaverin (120 mg) + 10 ml K (20 mmol) |
| 815 | 1:10:28 | 00.05.15 | 10:38:32 | K 100 ml/h (=200 mmol/h) |
| 1052 | 1:30:44 | 00.05.15 | 10.58:47 | K 50 ml/h (=100 mmol/h) |
| 1287 | 1:50:47 | 00.05.15 | 11:18:50 | K 20 ml/h (=40 mmol/h) |
| 1604 | 2:17:48 | 00.05.15 | 11:45:51 | go on bypass (2.5 L/min) |
| 1613 | 2:18:38 | 00.05.15 | 11:46:41 | stop K |
| 1653 | 2:22:01 | 00.05.15 | 11:50:04 | spontaneously heart beating |
| 1914 | 2:44:18 | 00.05.15 | 12:12:21 | Pump flow 0.5 L/min (weaning from bypass) |
| 2598 | 3:42:43 | 00.05.15 | 13:10:45 | off bypass |
| 3147 | 4:29:33 | 00.05.15 | 13:57:35 | normal urine production |

After the 6-hour test period, the animal was put to death with a euthanasia solution. The heart was examined visually for signs of disease (ischemia, congenital defects, emboli or thrombosis).

As appears from FIG. 1, which illustrates the time schedule for CPR with potassium chloride administration and A-V ECMO, the aortic pressure decreases during the CPR. After 1 h of CPR in combination with potassium administration followed by ECMO, the heart rhythm of the pig was reinstated and ROSC came into effect.

Figure 2:
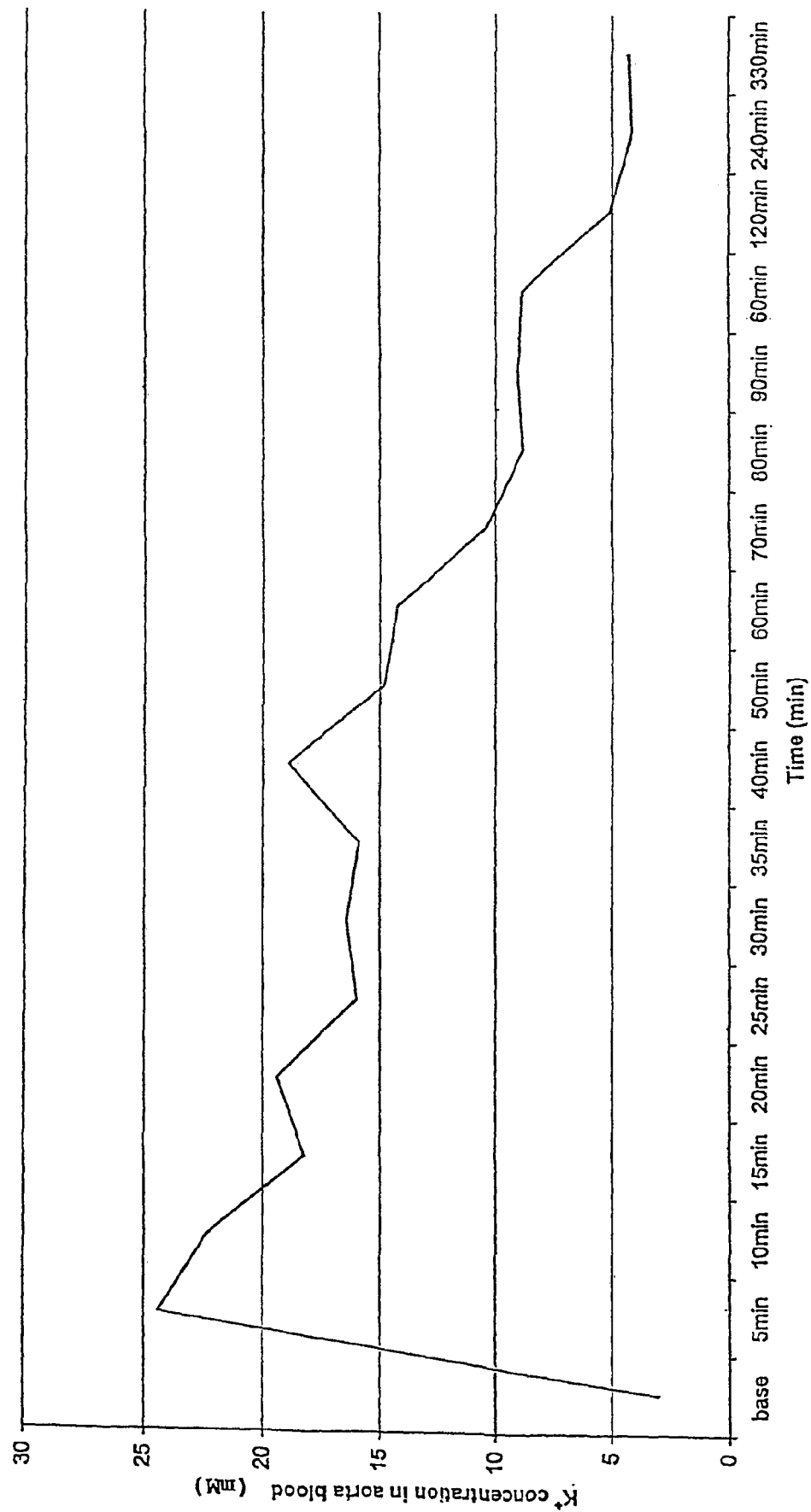
FIG. 2 illustrates the effect of CPR with potassium chloride and V-A ECMO on the potassium ion concentration in aortic blood.

In FIG. 2 the potassium ion concentration in aortic blood is shown during the experiment. After an initial potassium ion concentration peak due to the booster injection, the concentration is kept between 15 and 20 mM throughout the treatment period.

Even though the experiments performed above were made on pigs, the present invention also apply on humans due to their anatomic and physiological similarities. However, some of the experimental parameters above have to be adapted for human treatment due to the differences in blood volume, body weight etc.

The invention claimed is:

1. A method for the prevention of stone heart development during acute cardiac ventricular fibrillation in connection with cardiopulmonary resuscitation, comprising
   administering potassium ions in a cardioplegic solution to a patient during prolonged CPR, in an amount effective to obtain cardioplegia, wherein said cardioplegic solution is providing by dissolving said potassium ions in a pharmaceutically acceptable medium in a concentration of 12-30 mM when the potassium ions are injected as a booster solution directly into the heart, and in a concentration of 12-140 mM when the potassium ions are administered as an infusion solution.

2. Method according to claim 1, wherein potassium in the form of a salt with one or more anions selected from the group consisting of chloride, acetate, lactate, phosphate, carbonate, and bicarbonate is dissolved in the pharmaceutically acceptable medium, optionally together with a vasodilator.

3. Method according to claim 2, wherein the potassium ion concentration is 16-22 mM when the cardioplegic solution is injected as a booster solution directly into the heart.

4. Method according to claim 2, wherein potassium chloride is dissolved.

5. Method according to claim 2, wherein the vasodilator is present and is selected from the group consisting of papaverin, nifedipin, nitroglycerine, nitroprusside, and magnesium.

6. The method according to claim 2, wherein the pharmaceutically acceptable medium is water.

7. Method according to claim 1, wherein the cardioplegic solution is administered as a booster solution via direct injection into the coronary vessels, or into the left ventricle, followed by continuous administration of the cardioplegic solution; or infusion via a central venous catheter into the right atrium, the right ventricle or arteria pulmonaris, wherein the potassium ion concentration is incrementally decreased while maintaining the potassium ion concentration in the patient's aortic blood between 15 and 20 mM.

8. Method according to claim 1, wherein the potassium ion concentration of the heart is decreased after the end of the administration of the cardioplegic solution by infusion of a solution containing insulin and glucose.

9. Method according to claim 1, wherein the cardioplegic solution is administered to the patient during effective heart compressions.

10. Method according to claim 1 wherein said potassium ion concentration is 16-22 mM when the cardioplegic solution is injected as a booster solution directly into the heart.

11. The method of claim 5 wherein said vasodilator is 40-120 mg of papaverin.

12. Method according to claim 1, wherein the cardioplegic solution is administered as a booster solution via direct injection into the coronary vessels, or into the left ventricle, followed by continuous administration of the cardioplegic solution; or infusion via a central venous catheter into the right atrium, the right ventricle or arteria pulmonaris, wherein the potassium ion concentration is incrementally decreased to control the potassium ion concentration when reaching the heart to be 12-30 mM.

* * * * *

UNITED STATES PATENT AND TRADEMARK OFFICE
CERTIFICATE OF CORRECTION

| | |
|---|---|
| PATENT NO. | : 7,270,833 B2 |
| APPLICATION NO. | : 10/344038 |
| DATED | : September 18, 2007 |
| INVENTOR(S) | : Stig Steen |

It is certified that error appears in the above-identified patent and that said Letters Patent is hereby corrected as shown below:

In claim 1, column 8, line 59, delete "providing" and insert --provided--.

Signed and Sealed this

First Day of June, 2010

David J. Kappos
*Director of the United States Patent and Trademark Office*